United States Patent
Calfee et al.

(10) Patent No.: US 6,391,149 B1
(45) Date of Patent: May 21, 2002

(54) METHOD AND APPARATUS FOR CONCENTRATING A SOLUTE IN SOLUTION WITH A SOLVENT

(75) Inventors: Richard V. Calfee, Houston; Kenneth M. Bueche, Friendswood, both of TX (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/090,891

(22) Filed: Jun. 4, 1998

(51) Int. Cl.[7] .......................... B01D 1/16; C01B 25/234
(52) U.S. Cl. ............................... 159/47.1; 159/DIG. 12; 159/DIG. 19; 159/DIG. 20; 159/DIG. 37; 423/317; 423/321.1; 588/20
(58) Field of Search ................... 159/44, 47.1, 43.1, 159/DIG. 37, DIG. 16, DIG. 20, DIG. 12, DIG. 19, 47.3; 202/201, 203; 203/1–3, 100, 49; 588/20; 423/317, 321.1

(56) References Cited

U.S. PATENT DOCUMENTS

| | | | |
|---|---|---|---|
| 3,127,300 A | | 3/1964 | Maggio |
| 3,404,954 A | | 10/1968 | Jeffes et al. |
| 3,440,010 A | * | 4/1969 | Rushton .............. 159/DIG. 19 |
| 3,467,162 A | | 9/1969 | Putnam |
| 3,620,282 A | | 11/1971 | Newton .................... 159/13 C |
| 3,788,474 A | | 1/1974 | Granger et al. ............. 210/137 |
| 3,789,902 A | * | 2/1974 | Shah et al. .................... 159/49 |
| 3,839,159 A | | 10/1974 | Dunnavant et al. |
| 3,970,511 A | * | 7/1976 | Rat et al. .............. 159/DIG. 19 |
| 4,079,585 A | * | 3/1978 | Helleur ...................... 159/47.3 |
| 4,087,248 A | * | 5/1978 | Miles .......................... 23/230.6 |
| 4,090,129 A | * | 5/1978 | Gear .......................... 222/132 |
| 4,208,298 A | * | 6/1980 | Irie et al. ............. 159/DIG. 12 |
| 4,246,233 A | * | 1/1981 | Sheeline ...................... 422/159 |
| 4,300,393 A | * | 11/1981 | Stearns .................... 73/863.11 |
| 4,311,668 A | | 1/1982 | Solomon ...................... 422/70 |
| 4,383,887 A | | 5/1983 | Kuhnlein et al. ......... 159/13 A |
| 4,505,697 A | | 3/1985 | Lee et al. ..................... 494/35 |
| 4,794,086 A | | 12/1988 | Kasper et al. |
| 4,836,891 A | | 6/1989 | Files et al. |
| 4,846,935 A | | 7/1989 | Giesselmann et al. ........ 203/86 |
| 4,908,512 A | * | 3/1990 | Caprioli et al. ............. 250/281 |
| 4,959,122 A | * | 9/1990 | Kurematsu et al. ........ 159/47.3 |
| 5,004,522 A | * | 4/1991 | Koboshi et al. ............ 159/47.3 |
| 5,074,658 A | | 12/1991 | Tavlarides et al. ............ 356/73 |
| 5,098,657 A | | 3/1992 | Blackford et al. |
| 5,122,261 A | | 6/1992 | Hollingsworth ............. 209/170 |
| 5,294,003 A | | 3/1994 | Hollingsworth ............. 209/164 |
| 5,441,878 A | | 8/1995 | Thies et al. |
| 5,750,027 A | | 5/1998 | Allington et al. |

* cited by examiner

Primary Examiner—Virginia Manoharan
(74) Attorney, Agent, or Firm—Blakely, Sokoloff, Taylor & Zafman

(57) ABSTRACT

The present invention provides a method, and an apparatus, for forming a prescribed concentration of a substance in a mixture with a fluid, from a comparatively dilute mixture. The mixture is most preferably a solution of a solute in a solvent. The following summary and description generally discuss the invention in terms of a particularly preferred solution and a preferred use for that solution; however, in its broadest embodiments, the invention encompasses both the use for other solutions, and the use for a suspension of a solid substance in a fluid to form a mixture (which can also be referred to as a slurry). The invention provides for significant economic, safety and qualify benefits over conventional evaporative systems.

3 Claims, 10 Drawing Sheets

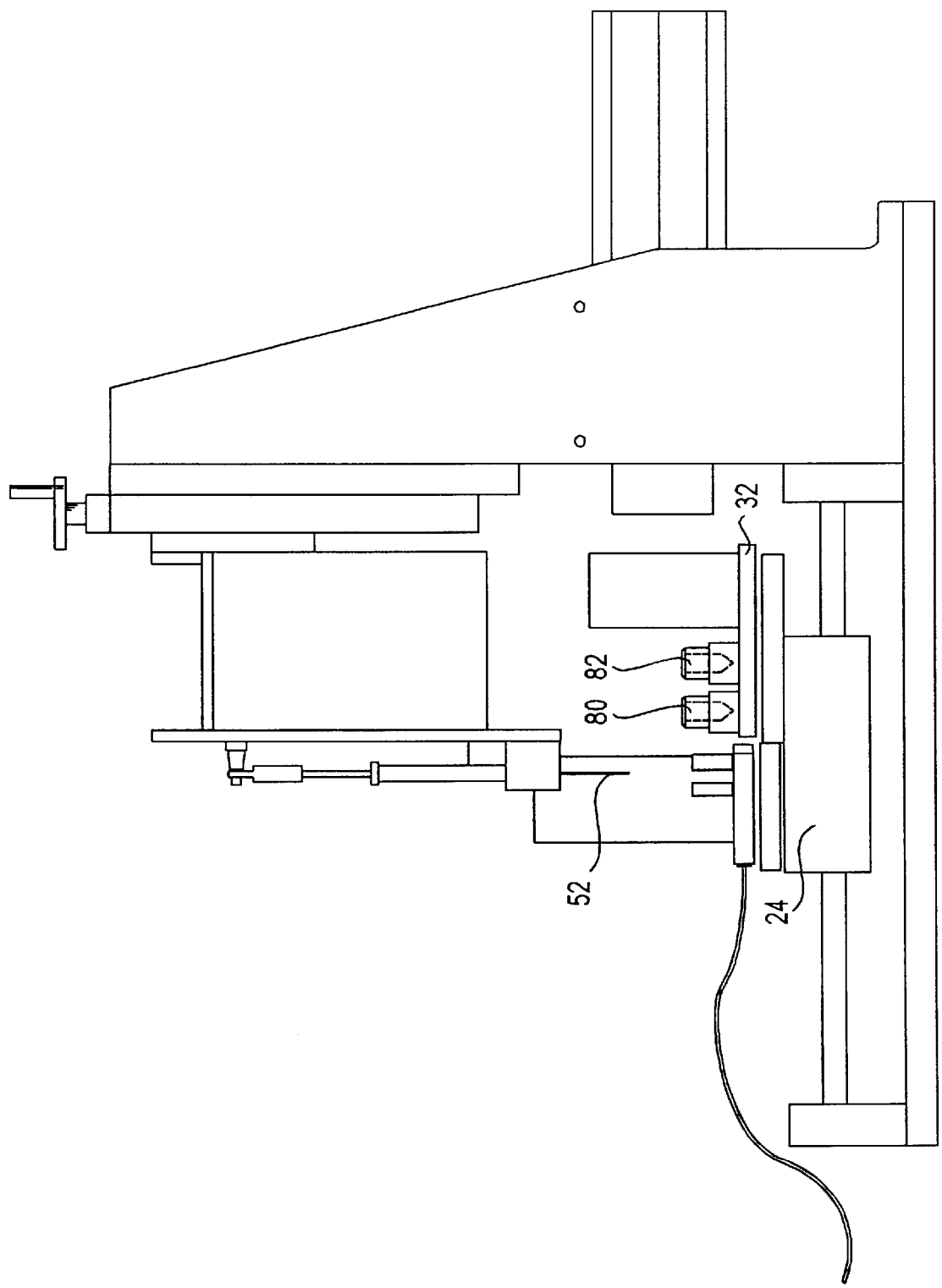

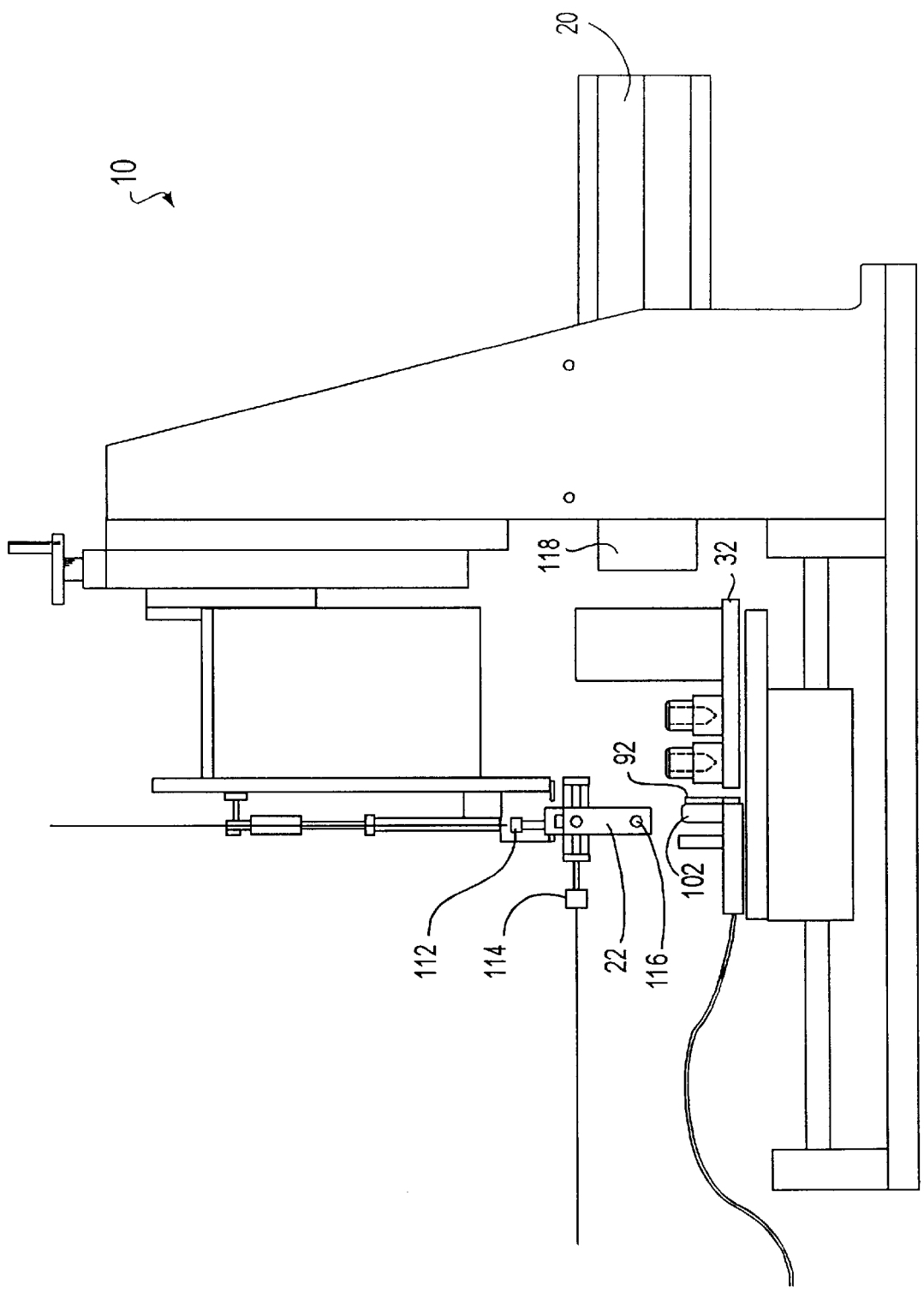

METHOD AND APPARATUS FOR CONCENTRATING A SOLUTE IN SOLUTION WITH A SOLVENT

BACKGROUND OF THE INVENTION

This invention relates generally to the production of concentrated solutions, and, more particularly, to a method and an apparatus for forming a concentrated solution, of a prescribed concentration of solute in a solvent, from a comparatively dilute solution.

Innumerable chemical applications require concentrated solutions of a solute dissolved in a solvent. Each application has unique requirements for the type of solute, the type of solvent, and the concentration of the solute in the solvent. Such solutions, however, are generally available only in a limited number of concentrations from traditional suppliers. The ability to vary a solution's concentration is therefore an important art for a wide variety of applications.

The concentration of a solution can be increased through the addition of more solute, or the evaporation of solvent from the solution. In the case of some solutions, such as radioactive solutions, additional solute is often not readily available, and thus the addition of more solute is not practicable. These solutions require evaporative concentration methods.

In conventional evaporative concentration methods, the solution is located in a container, such as a beaker. The solvent is then evaporated, preferably with the addition of heat, and the level of solution in the container thus goes down to an appropriate level for a smaller volume of solution. As the solution evaporates, solute precipitates out onto the container walls above the reduced level of the solution, leaving a crust of dry precipitate where the solution level receded. This precipitation removes solute from the solution, limiting both the efficiency and the accuracy of concentration. These problems are exacerbated when dealing with hazardous and/or costly solutions, such as solutions containing radioactive solutes, in that the quantity of precipitated solute is unknown, and it is difficult to efficiently recover the solute in a practical form.

Accordingly, there has existed a definite need for a method, and related apparatus, to concentrate a solute in solution with a solvent without significant precipitation of the solvent. The present invention fulfills this need and provides further related advantages.

SUMMARY OF THE INVENTION

The present invention provides a method, and an apparatus, for forming a prescribed concentration of a substance in a mixture with a fluid, from a comparatively dilute mixture. The mixture is most preferably a solution of a solute in a solvent. The following summary and description generally discuss the invention in terms of a particularly preferred solution and a preferred use for that solution; however, in its broadest embodiments, the invention encompasses both the use for other solutions, and the use for a suspension of a solid substance in a fluid to form a mixture (which can also be referred to as a slurry). The invention provides for significant economic, safety and quality benefits over conventional evaporative systems.

The apparatus of the invention features a syringe configured to pass the dilute solution through an orifice to form a suspended globule (such as a droplet) of the dilute solution from which solvent is evaporated. The apparatus is configured such that the suspended globule is in contact with sufficiently little solid material to avoid significant precipitation and plating of solute as the solvent evaporates. Preferably, the solution becomes suspended as a drop hanging by surface tension forces from a flat, horizontal, contact surface surrounding the orifice. The orifice adjoins a narrow passageway that is configured to substantially prevent concentration gradient diffusion from the evaporating dilute solution as it becomes concentrated. The apparatus of the invention preferably also features a measuring device, such as a laser micrometer, configured to gauge the amount of suspended solution, as well as a heater configured to provide a stream of heated gas to the suspended solution to accelerate the evaporation of solvent from the solution.

The inventive method and apparatus provide significant advantages over known methods and apparatus, such as the known method of simply evaporating solvent from a solution contained in a container. For the inventive method and apparatus, the suspended solution has little contact with a solid contact surface, thus minimizing the solid surface on which plating can occur. Furthermore, the area of contact is substantially constant, and thus remains wet. This advantage is particularly beneficial when the relevant solution is difficult to handle, such as is the case for radioactive solutions.

The invention also features monitoring the size of the suspended solution, and further features passing additional dilute solution from the orifice to maintain the size of the drop between a prescribed minimum size and a prescribed maximum size, during evaporation of the solvent. The monitoring and emission continue until the drop has reached the prescribed concentration. These features advantageously provide for the concentration of substantially larger quantities of solution to substantially higher concentration levels within the natural limitations on drop size (i.e., the limitations on the amount of weight that the surface tension forces can support). These features also provide for little to no precipitation losses of solute during evaporation of the solvent.

Additionally, the invention features a computerized control system that, in combination with the syringe, the measuring device and the heater, advantageously provides for the production of extremely accurate quantities of solution that are concentrated to very specific concentrations.

Other features and advantages of the invention will become apparent from the following detailed description, taken in conjunction with the accompanying drawings, which illustrate, by way of example, the principles of the invention.

BRIEF DESCRIPTION OF THE DRAWINGS

FIG. 2A is a front elevational view of the apparatus depicted in FIG. 1A, with a laser micrometer and a pick-off device not depicted to better depict the devices behind the laser micrometer and pick-off device.

FIG. 5A is a front elevational view of the apparatus depicted in FIG. 1A, with a final-evaporation port of a heater directly below a source, and with a laser micrometer not depicted to better depict the devices behind the laser micrometer.

DETAILED DESCRIPTION OF THE PREFERRED EMBODIMENTS

Figure 1A:
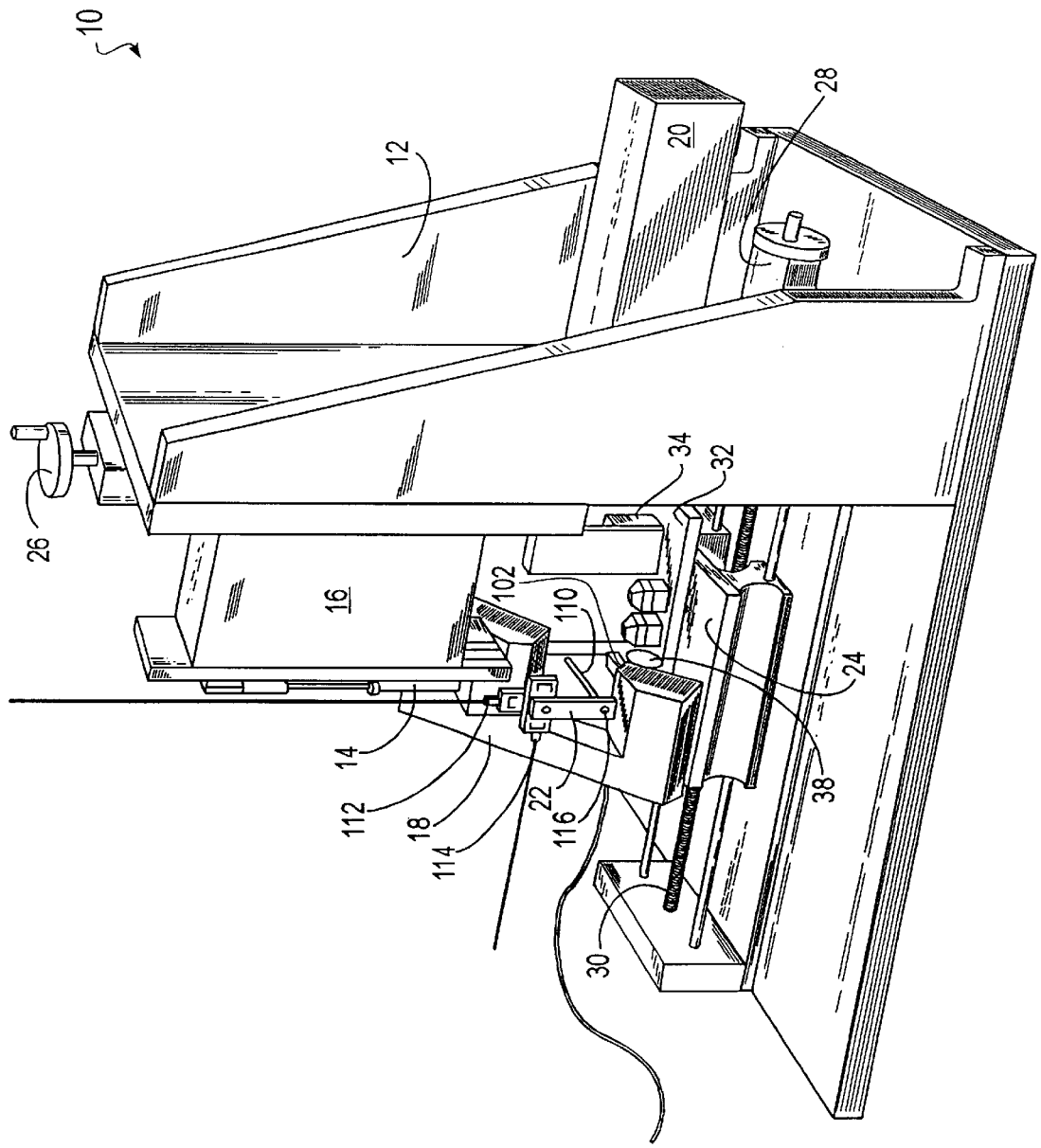
FIG. 1A is a perspective view of an apparatus for concentrating an amount of solute in solution, embodying features of the present invention.
Figure 1B:
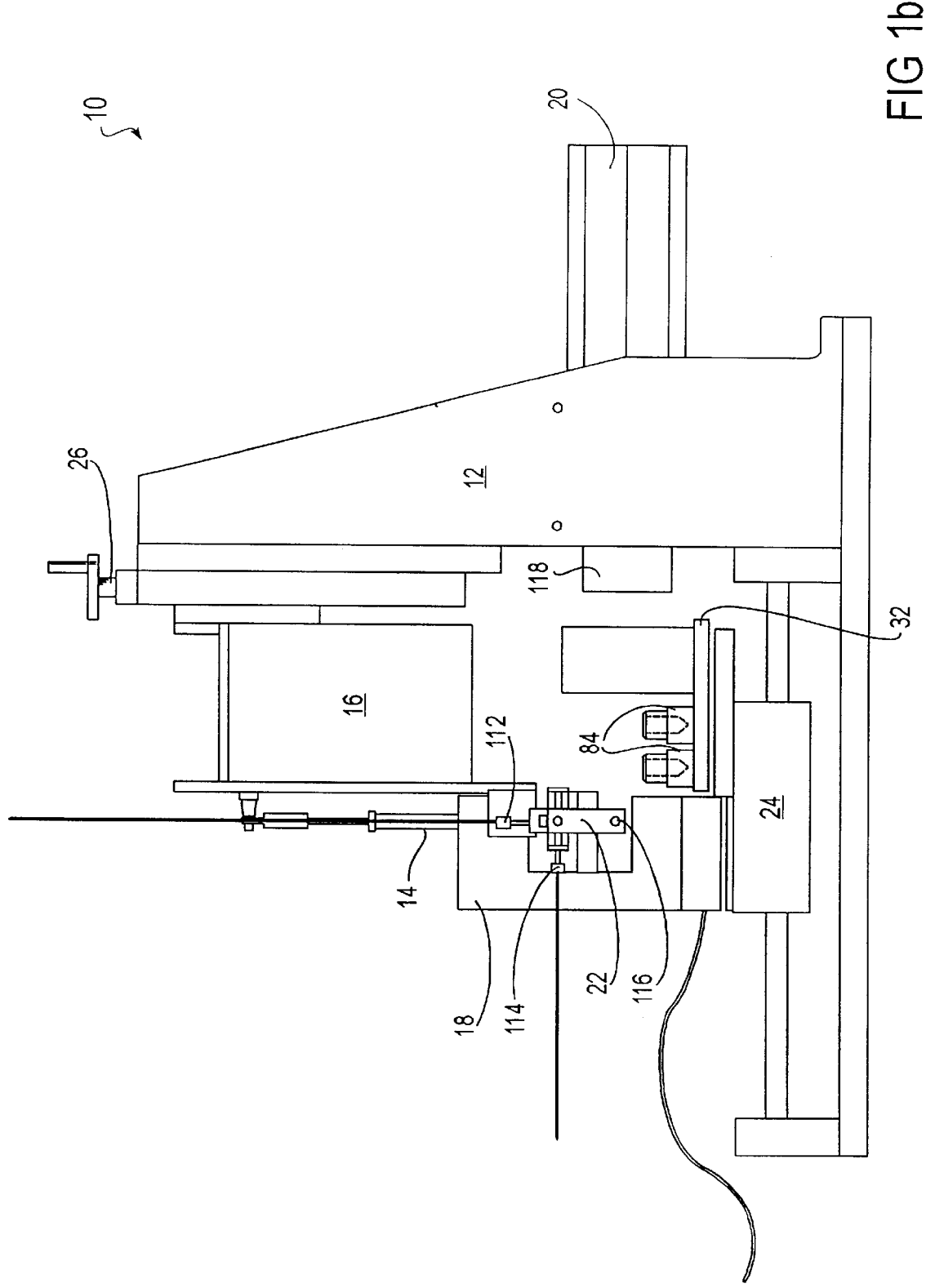
FIG. 1B is a front elevational view of the apparatus depicted in FIG. 1A.
Figure 1C:
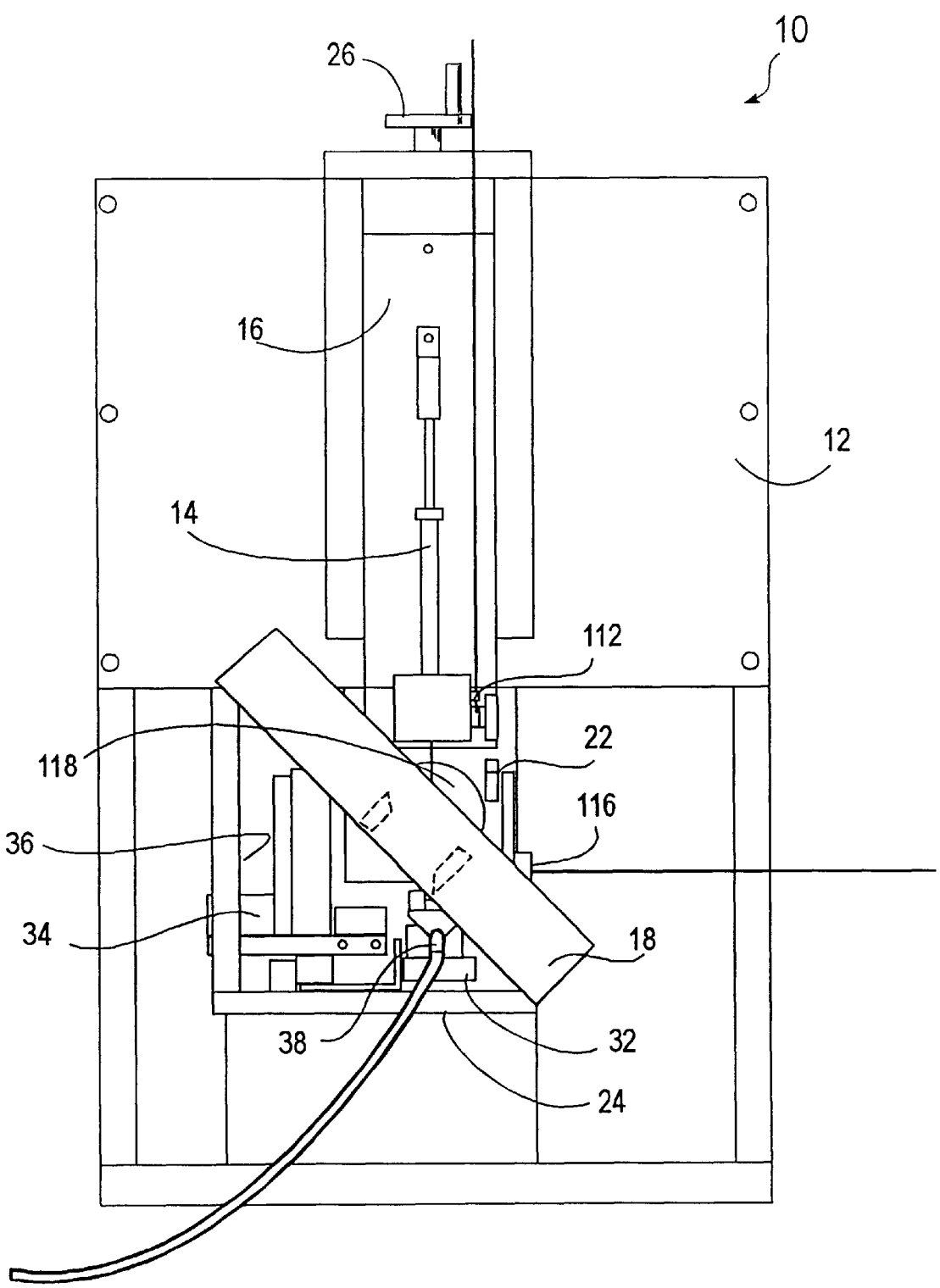
FIG. 1C is a left side elevational view of the apparatus depicted in FIG. 1A.

An apparatus 10 for forming a concentrated solution, from a comparatively dilute solution, according to the present invention, is shown in FIGS. 1A–1C. The apparatus is useful in concentrating a solution to a prescribed concentration level from a comparatively dilute concentration level. The apparatus is particularly useful for concentrating a solute that is costly, hazardous, and/or particularly susceptible to precipitating and plating onto a solid surface, to a prescribed concentration of solute in a solvent, and most particularly to concentrations in a solvent that entail the evaporation of a comparatively large portion of the solution.

One such solution is radioactive orthophosphoric acid in a water solvent. The apparatus is further useful for providing the concentrated solution in a suspended drop that can be used to form a substantially uniform plated coating of solute within a source, which is preferably a tubular device for receiving the solute. The resulting source, being coated with the radioactive solute, provides a useful radiation source for intravascular radiotherapy in the prevention of restinosis following percutaneous transluminal angioplasty, as described in U.S. Pat. No. 5,199,939, which is incorporated herein by reference.

The apparatus 10 includes a frame 12 carrying a vertically oriented syringe 14, a stepper motor 16, a laser micrometer 18, a high-resolution camera 20, a pick-off device 22, and a table 24. A manual syringe-adjuster 26 is configured to vertically adjust the position of the syringe with respect to the frame. The stepper motor connects to both the frame and the syringe, being configured to actuate the syringe to form a drop-sized quantity of solution, the size of which can be measured by the laser micrometer. Preferably the laser micrometer is configured to measure the drop at an angle to better adapt to the changing configuration of the drop at different sizes.

A Model 50300 pump, available from the Kloehn Company, Inc., of Las Vegas, Nev., provides a suitable stepper motor configured to be used with a syringe, where the stepper motor is controllable by a computer through an RS-232 interface. An LS-3100 Series Laser Scan Micrometer, available from the Keyence Corporation of America, of Saddle Brook N.J., provides a suitable laser micrometer, and is capable of doing 400 scans per second at a measurement precision of ±2 μm.

Vertical, in the context of this embodiment, generally refers to a gravity-based reference frame defining the direction of forces necessary to suspend a drop of the solution from the syringe. However, for an appropriate embodiment it can be considered equivalent to reference frames relevant to defining the forces necessary to suspend the solution. For example, a drop hanging from a spinning embodiment will exhibit "centrifugal force" effects, and thus will have a partially momentum-based reference frame.

Figure 2B:
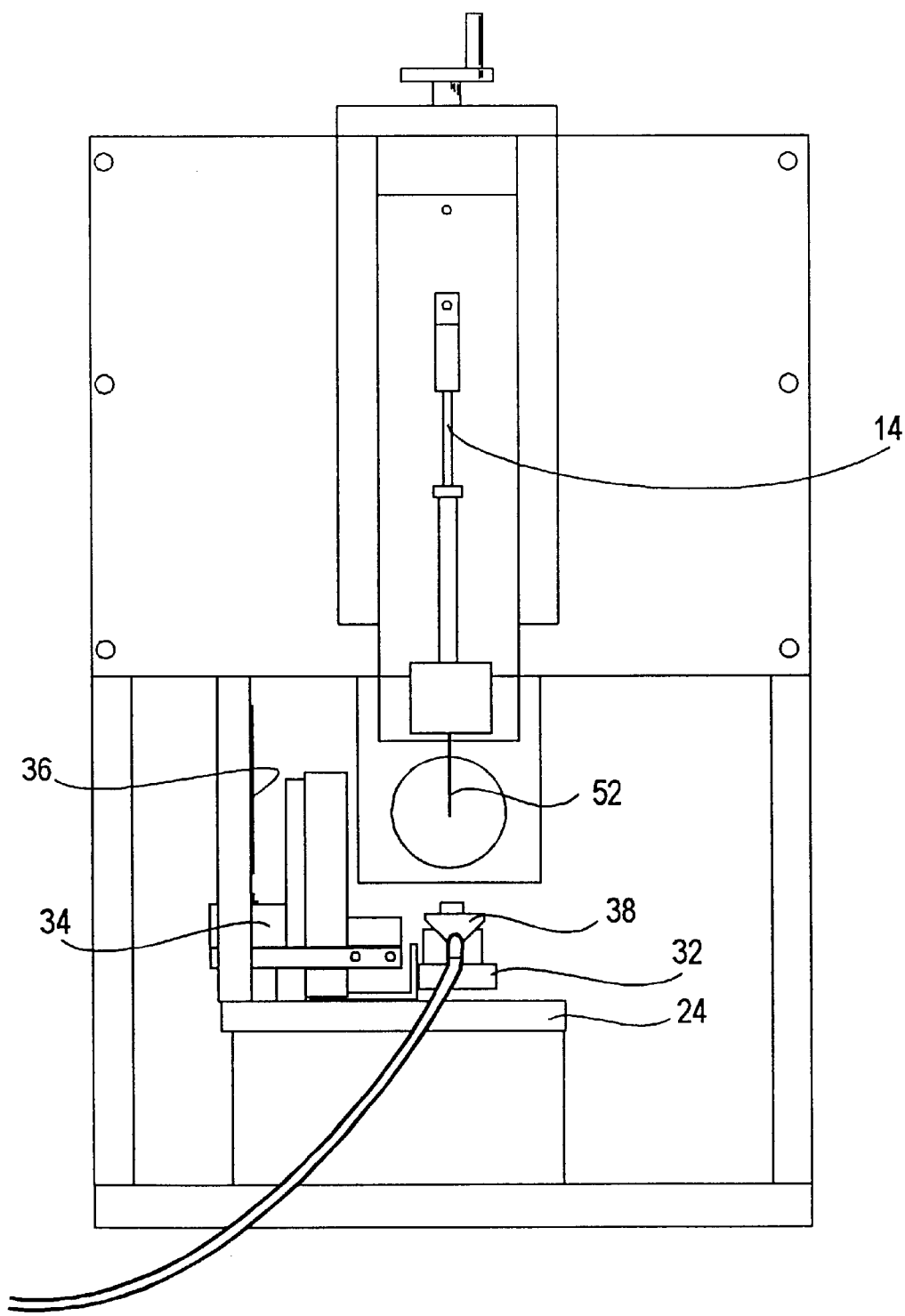
FIG. 2B is a side elevational view of the apparatus depicted in FIG. 2A.

As seen in FIGS. 2A–2B, which depict the apparatus of FIGS. 1A–1C with the laser micrometer 18 and the pick-off device 22 removed, a first motor 28 is configured to laterally adjust the position of the table 24 with respect to the frame by way of a first screw drive 30 (see FIG. 1A). The table carries a platter 32, which is vertically adjusted with respect to the table by a second motor 34, in cooperation with a second screw drive 36. The table also carries a heater 38 configured to heat and evaporate a drop of solution suspended from the syringe 14 to concentrate the solution, and further configured to heat the concentrated solution after it has been loaded into a source, evaporating the solvent and plating the solute onto the source.

The apparatus further includes a computerized control system (not shown) configured to control the first motor 28, the second motor 34, the stepper motor. 16 and the heater 38. The control system can be further configured to control all other controllable aspects of the apparatus, such as the syringe-adjuster 26, and any related production devices.

Figure 3C:
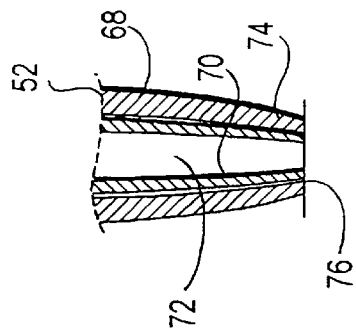
FIG. 3C is a partial, cross-sectional, elevational view of a lower tip of the syringe depicted in FIG. 3A.
Figure 3B:
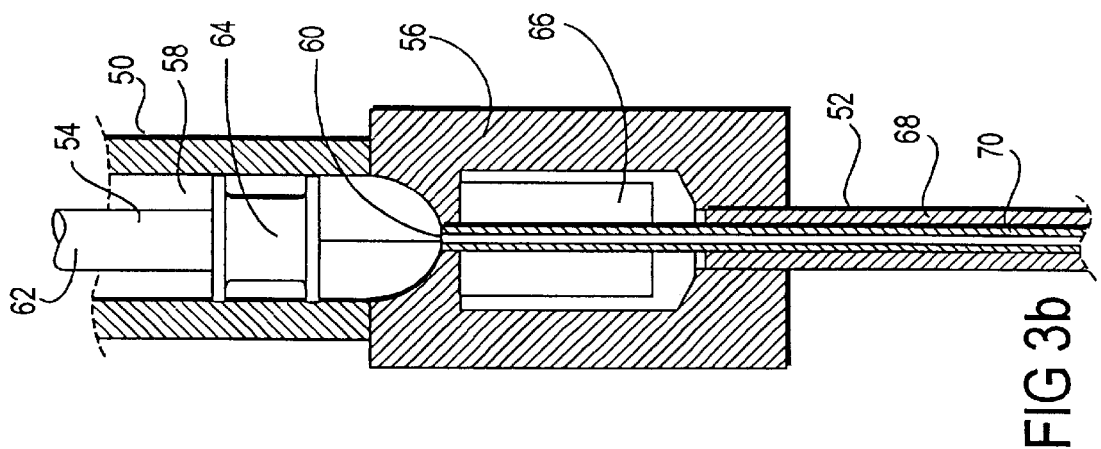
FIG. 3B is a partial, cross-sectional, elevational view of a mid-portion of the syringe depicted in FIG. 3A.
Figure 3A:
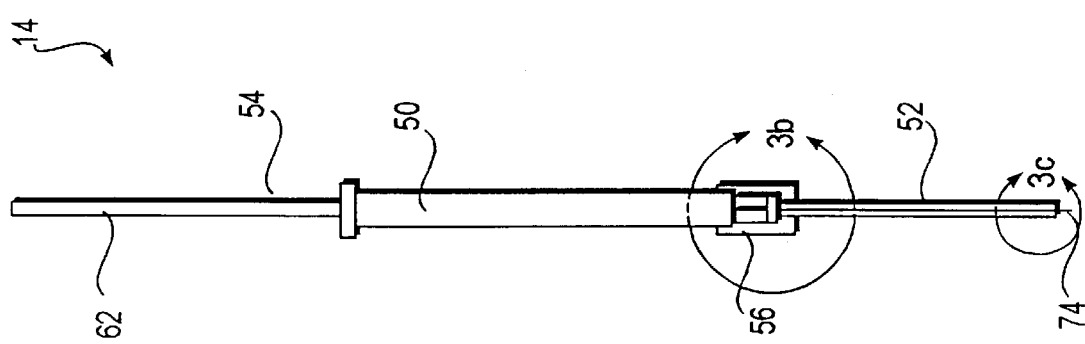
FIG. 3A is an elevational view of a syringe used in the apparatus depicted in FIG. 1A.

As seen in FIGS. 3A–3C, the syringe 14 includes a vertically oriented body 50, a vertically oriented needle 52, a vertically oriented plunger 54, and a mounting hub 56 configured to mount the syringe's body and needle to the frame 12. The syringe body is configured in the standard form of a syringe, having a cylindrical chamber 58 with a consistent cross section extending down to a bottom end, where the chamber rounds down to a small opening 60. The syringe body is preferably transparent, having striations (not shown) indicating the volume of the chamber from the point of the striation down to the small opening. The striations serve to allow an operator of the system to visually verify the proper functioning of the syringe.

The plunger 54 includes a shaft 62 that can be driven into and out of the syringe body's chamber 58 by the stepper motor 16. A head 64 is affixed to a bottom end of the shaft, and is situated within the chamber. The head conforms to the cross section of the chamber, forming an airtight seal between the head and the chamber as the head slides up and down the chamber, motivated by the shaft. The plunger, driven by the stepper motor, thus acts as a piston, capable of drawing a fluid through the small opening 60 and into the chamber, and driving a fluid through the small opening and out of the chamber, by moving up and down with respect to the chamber.

At any given position within the chamber 58, the plunger head 64 therefore forms an enclosed cavity within the chamber, the cavity being open only through the small opening 60. Advancing the plunger into the chamber reduces the cavity's volume, driving the contents of the cavity out through the small opening. When the plunger is fully advanced down into the chamber, the cavity's volume is lowered to essentially zero, and the cavity is emptied of substantially all fluid or gas through the small opening. A fully advanced plunger, therefore, effectively evacuates the syringe. Retracting the plunger from the chamber increases the volume of the cavity, thus drawing fluid or gas into the cavity.

The mounting hub 56 is a block-like structure, an upper end of which conformingly receives the lower end of the syringe body 50, holding the syringe body rigidly in place relative to the frame. An adhesive such as epoxy is used to bond the syringe body to the mounting hub. The mounting hub defines a hollow shaft 66 providing a corridor for the needle 52 to extend down from the chambers small opening 60.

The needle 52 has both an outer shell 68, and a concentric, hollow inner tube 70 extending through the outer shell. An upper end of the inner tube is affixed to the syringe body, such as by epoxy. It is affixed to the small opening of the syringe body, providing a vertical passage 72 in communication with the chamber through the small opening. The inner tube extends down from the small opening 60 to a lower tip 74 of the needle. The passage has a generally constant cross sectional area, which necks down to form an orifice at the lower tip of the needle. The orifice preferably ranges from 0.005 in. to 0.010 in. in diameter.

The needle's outer shell 68 extends from the lower tip 74 of the needle 52, up to a lower end of the mounting hub 56. The outer shell has a generally consistent cross section that necks down at its lower end to merge with the inner tube's lower end, forming the lower tip of the needle. The needle's outer shell is affixed to the lower end of the mounting hub, such as with epoxy, providing structural support to the needle and holding the needle rigidly in place relative to the frame 12 and the syringe body 50.

The needle's lower tip 74 provides a contact surface 76 that is preferably not convex, and that is most preferably substantially flat and horizontal, the contact surface including both the lower end of the inner tube 70 and the lower end of the outer shell 68. This horizontal contact surface is smooth, providing a substantial area to support a drop at the lower tip of the needle 52. Thus, the syringe 14 forms a container, having an orifice at the needles lower tip, and being configured to pass fluids from within the container out through the orifice.

Preferably, the contact surface has a diameter ranging between 0.030 in. and 0.090 in. As the size of the contact surface increases, the stability of a drop suspended from the contact surface increases. However, the final concentrated size of a drop hanging from the contact surface can be reduced from its original size, and thus, after concentration, a larger contact surface may cause the drop to be difficult to see. Furthermore, a larger contact surface can lead to surface tension forces that make it difficult to remove the drop from the contact surface.

While the above-described components of the syringe 14 are preferred, a wide variety of components fall within the definition of, or are equivalent to, a syringe. In particular, a syringe as claimed could be embodied in any device that can controllably pass a substance from a chamber out of an orifice, where the emission of the substance is controllable. Likewise, for syringes having a body, a needle, and a plunger, a wide variety of configurations are within the scope of the invention. For example, a horizontally oriented body, a plunger and a needle, that can provide the same essential functions of the vertical syringe, fall within the scope of the invention.

Components that are to come into contact with the solution, and particularly with the solution after it has been concentrated, are preferably made of materials compatible with the solution. Thus, the needle 52 and the body 50 are preferably made from quartz.

Retuning to FIGS. 1A and 2A–2B, the table 24 is configured to be laterally positionable vertically below the needle 52. The first motor 28 can laterally adjust the table's position, by use of the screw drive 30, so as to place either the heater 38 or the platter 32 directly below the needle. The platter is configured to carry a plurality of vessels, such as vials, each of which can be laterally positioned directly under the needle by the first motor. A first vial 80 of the plurality of vessels contains a fluid for flushing the syringe 14, such as the solvent, water. A second vial 82 of the plurality of vessels contains a dilute solute in solvent, such as dilute radioactive orthophosphoric acid in water.

Preferably, the vials 80, 82 are received in spring-loaded bays 84 in the platter 32. The spring-loaded bays provide protection against the needle 52 breaking if it strikes the bottom of one of the vials.

The heater 38, which is configured to heat a drop of fluid suspended from the lower tip 74 of the needle 52, can be of a wide variety of designs. Preferably the heater is configured to heat and evaporate the drop by creating a column of heated gas flowing up and around the drop. The gas can be air or any other substance that would allow and encourage the evaporation of the solvent. Preferably the gas is an inert gas such as nitrogen. The gas is heated to a sufficient level to encourage the evaporation of the solvent.

For example, the heater can be a vertically oriented coil of a resistor wire, which can be heated by the application of a voltage across the wire. Such a heater heats the air in the vicinity of the wire, which then rises through the cooler surrounding air to form a column of heated air.

Figure 4C:
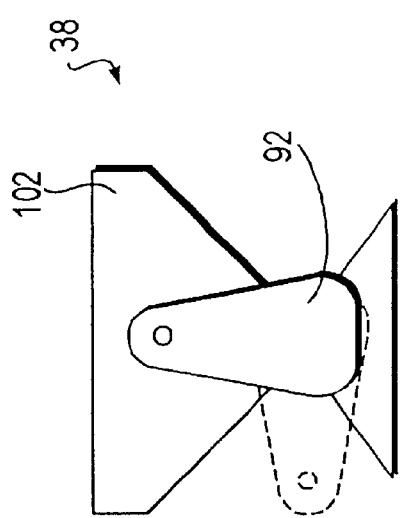
FIG. 4C is a side elevational view of the heater depicted in FIG. 4A.
Figure 4B:
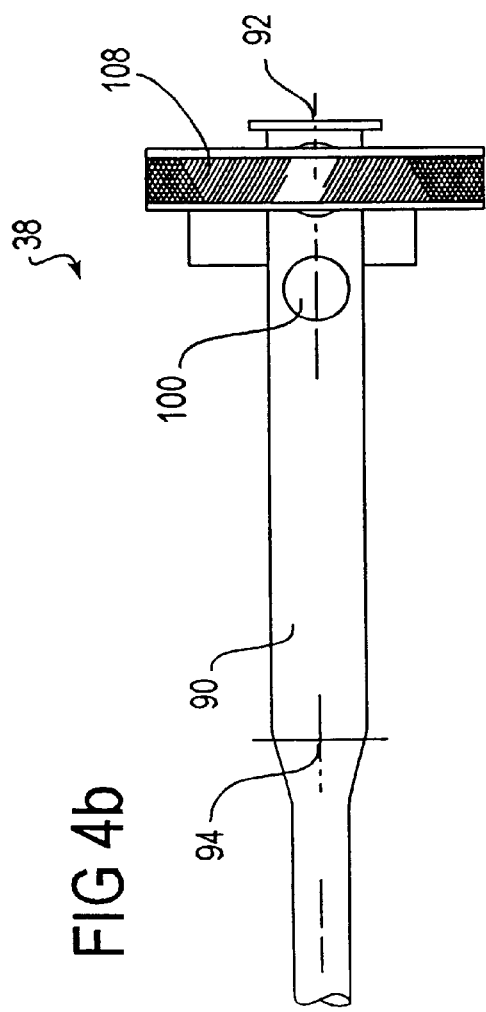
FIG. 4B is a plan view of the heater depicted in FIG. 4A.
Figure 4A:
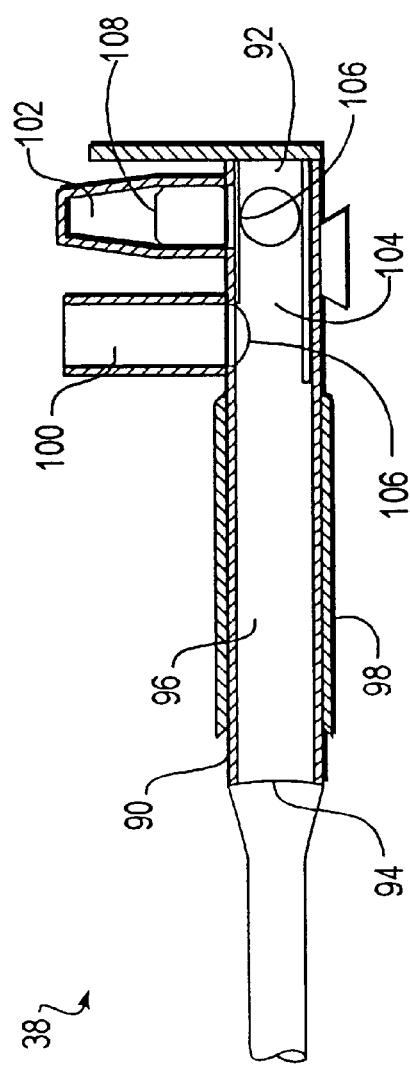
FIG. 4A is a cross-sectional elevational view of a heater used in the apparatus depicted in FIG. 1A, taken along line 4—4 of FIG. 2A.

A preferred heater, as seen in FIGS. 4A–4C, includes a body 90 and a valve 92. An inlet 94 on the body is configured to receive expanding gas, preferably being nitrogen, from a pressurized supply (not shown). Gas received by the inlet expands through a tubular main passage 96, which is partially surrounded by a heater element 98, preferably being a nichrome wire spiraled along the outside of the body, the wire being encased in a high-temperature epoxy. Passing through the main passage, the gas is directed by the valve through one of two ports, being a concentration port 100 and a final-evaporation port 102.

The valve 92 includes a tubular portion 104, the exterior of which conforms to the interior of the heater body's main passage 96 so as to receive the gas into the valve. Two holes 106 in the valve's tubular portion are configured to allow the gas to pass through only one port 100, 102 at a time, which can be selected by rotationally positioning the valve to align one hole with the selected port. The valve can be manually operated, or can be configured to be controlled by the computerized control system.

The concentration port 100 is a round vertical tube configured to form a column of air having an approximately round cross section when the heater 38 is activated. The final-evaporation port 102 is configured to form a column of air having a band-shaped cross-section, having a larger dimension and a smaller dimension. The final-evaporation port includes a diffusion screen 108 to produce a column of heated air having a more even distribution of heat over its cross-section.

Figure 5B:
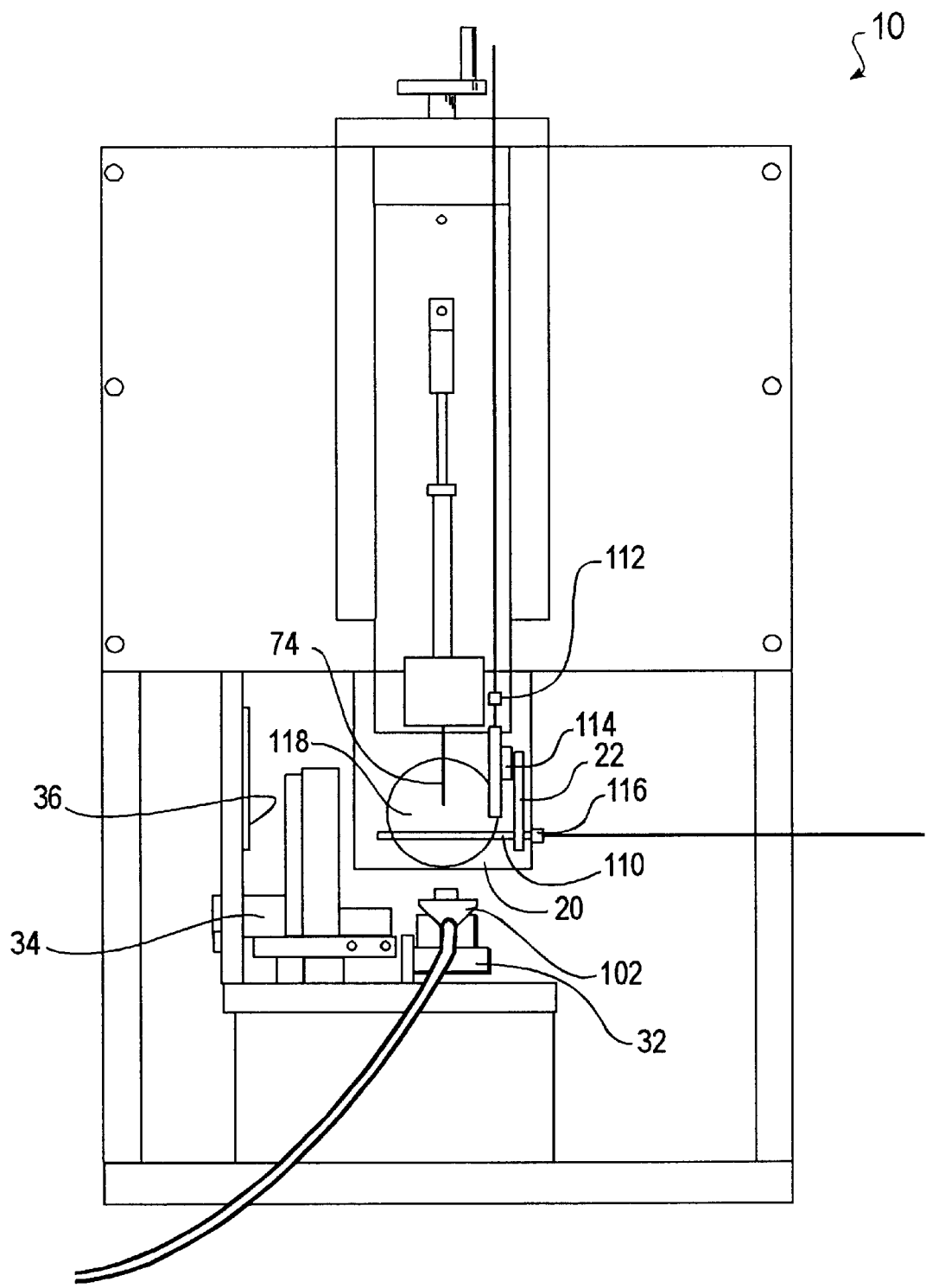
FIG. 5B is a side elevational view of the apparatus depicted in FIG. 5A.

As seen in FIGS. 1A–1C, as well as FIGS. 5A–5B, the pick-off device 22 is configured to retain a source 110, being a preferably tubular appliance configured to receive the drop of concentrated solution after the process of concentrating the solution on the syringe is complete. The pick-off device is further configured to position and move the retained source, while moving into contact with the drop to receive the drop from the syringe. For proper positioning, the pick-off device includes a top adjustment screw 112, a side adjustment screw 114, and a front adjustment screw 116. For use with radioactive solutions, these screws can include long shafts so that they can be used from outside of a radiation shield (not shown) around the apparatus 10.

The source 110, which can take numerous forms, preferably takes the form of a thin hollow tube perforated with a plurality of holes, the tube being configured to draw a drop of fluid into the tube with capillary forces. Preferably, the source is sized to precisely contain one drop of solution.

The high-resolution camera 20 is equipped with a zoom lens 118, and is configured to image a drop of fluid being suspended from the needle's lower tip 74. The image can be displayed on a monitor (not shown) for an operator of the apparatus 10. The camera's configuration can also image the source 110.

Figure 6A:
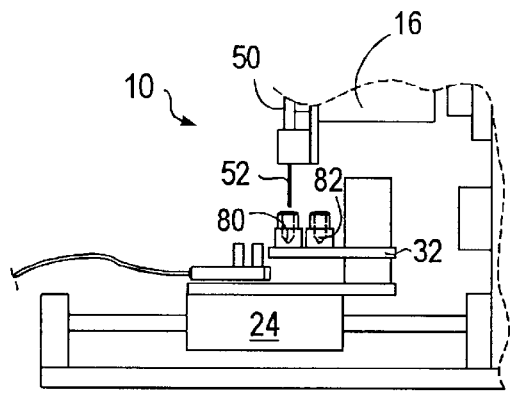
FIG. 6A is a front elevational view of the apparatus depicted in FIG. 2A, with a first vial entirely below a needle.
Figure 6B:
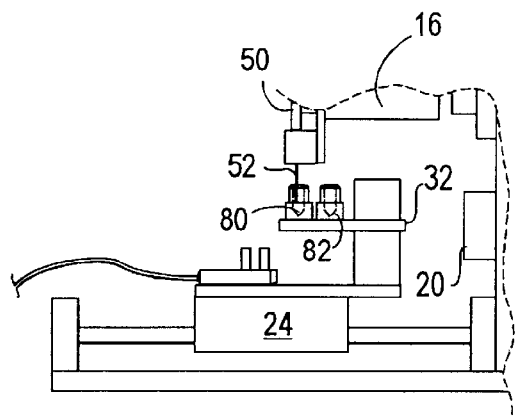
FIG. 6B is a front elevational view of the apparatus depicted in FIG. 6A, with the needle extending fully into the first vial.

Under the power of the second motor 34, the platter 32 is configured to vertically move the plurality vials with respect to the syringe 14. Using the second screw drive 36, the platter can be raised by the second motor such that the needle 52 extends fully into a vial that is located directly below the needle, as can be seen in FIG. 6B. Likewise, the platter can be lowered such that a vial directly under the needle is entirely below the lower tip 74 of the needle, as seen in FIG. 6A, allowing the vials to pass laterally below the needle without contacting the needle. It is preferable that the platter is configured to lower to a level that is convenient for positioning and removing vials without significant risk of the vials hitting the needle, such as the level depicted in FIG. 2A.

As seen in FIGS. 1A–1C and 2A–2B, a method embodying the present invention for concentrating the amount of a solute in solution with a solvent to a prescribed concentration begins by setting up the above described apparatus and adjusting it for use. In particular, the syringe-adjuster 26 is actuated to vertically adjust the position of the syringe such that the lower tip 74 of the needle 52 resides slightly above the measurement zone of the laser micrometer 18, thus configuring the laser micrometer to measure the size of a drop of solution suspended from the needle while the drop is still hanging from the needle. The stepper motor 16 fully advances the plunger 54 into the syringe body 50 to minimize the chamber size and effectively evacuate the syringe.

Additionally, the heater valve 92 is adjusted to direct the heated gas through the concentration port 100. The source 110 is mounted and retained in the pick-off device 22 (as seen in FIG. 5B), which is adjusted by its adjustment screws to hold the source in close proximity to the needle for fast and convenient use after the solution has been concentrated by the syringe 14. This position, however, must be selected to not interfere with the operation of the apparatus' components, such as the laser micrometer 18. Two vials are positioned on the platter 32. The first vial 80 contains a solvent, such as water, to be used for flushing the syringe. The second vial 82 contains a dilute solution of a solute in a solvent, preferably being the same solvent as is contained in solution in the first vial.

With the apparatus 10 set up and adjusted, it is optionally (and preferably) flushed and tested prior to evaporatively concentrating the solution. The plunger 54 is withdrawn from the syringe body 50 by the stepper motor 16 to cause a predetermined amount of air to be drawn into the cavity of the chamber 58. The table 24, with the platter 32 adjusted such that the vials 80, 82 are low enough to pass laterally below the needle 52, is laterally adjusted to place the first vial 80 directly below the needle, as seen in FIG. 6A. FIGS. 6A–6E do not depict the laser micrometer and a pick-off device to better illustrate the positions of the underlying parts of the apparatus 10.

Figure 6C:
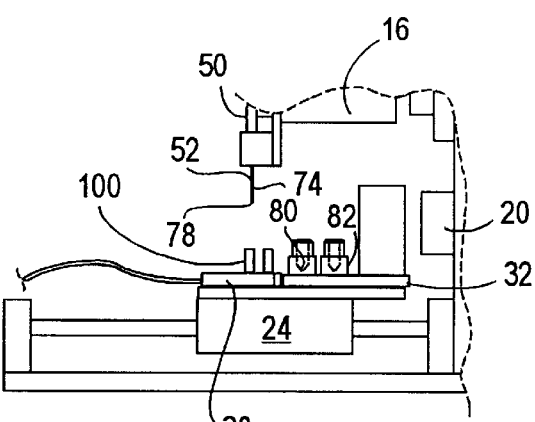
FIG. 6C is a front elevational view of the apparatus depicted in FIG. 6A, with a concentration port of a heater directly below the needle.
Figure 6D:
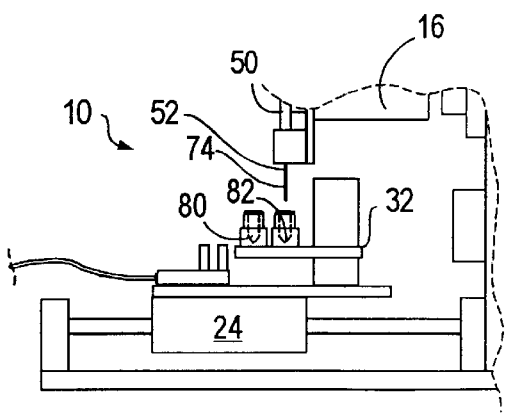
FIG. 6D is a front elevational view of the apparatus depicted in FIG. 6A, with a second vial entirely below the needle.
Figure 6E:
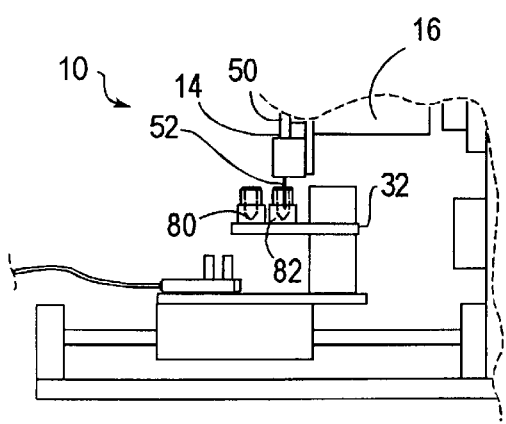
FIG. 6E is a front elevational view of the apparatus depicted in FIG. 6A, with the needle extending fully into the second vial.

The first vial 80 is vertically adjusted such that the needle 52 extends into the first vial, and into the solvent therein, as seen in FIG. 6B. The stepper motor 16 further withdraws the plunger 54 from the syringe body 50 by a calculated amount, making the chamber 58 larger, and thus drawing a predetermined quantity of the solvent from the first vial into the syringe chamber. The platter 32 is then lowered to a position low enough to allow the vials to pass under the needle. Preferably, the platter is lowered to its lowest position, where it cannot interfere with the operation of the laser micrometer 18 or the view of the camera 20. The table 24 is then moved longitudinally such that the concentration port 100 of the heater 38 is directly below the needle, as seen in FIG. 6C.

The solvent in the syringe chamber 58 is then evaporated down to the volume of a drop, using the same evaporation method as is described in more detail below for evaporatively concentrating the solution in the second vial 82. The solvent is passed out of the needle to form a drop suspended from the needle; the drop size is measured; some of the solvent is evaporated; and the volume of the drop is replenished to maintain the drop's size. When the solvent in the syringe chamber is preferably reduced to a single drop, the table is moved longitudinally and vertically to a position such that the plunger can be advanced fully into the chamber to eject the remaining drop of solvent back into the first vial, such as the position depicted in FIG. 6A.

After the apparatus 10 is set up and adjusted, and after it is optionally flushed and tested, a procedure similar to the flush and test procedure is used to evaporatively concentrate the solution in the second vial 82. The plunger 54, which is fully advanced into the syringe body 50, is withdrawn from the syringe body by the stepper motor 16 to cause a predetermined amount of air to be drawn into the cavity. Naturally, in the parlance of this application, air can be any environment deemed preferable to conduct the procedure. The table 24, with the platter 32 adjusted such that the vials 80, 82 are low enough to pass laterally below the needle 52, is laterally adjusted to place the second vial directly below the needle, as seen in FIG. 6D.

The second vial 82 is vertically adjusted such that the needle 52 extends into the dilute solution in the second vial to a depth adequate to draw a predetermined quantity of solution from the vial, as seen in FIG. 6E. The stepper motor 16 further withdraws the plunger 54 from the syringe body 50 by an amount selected to draw the predetermined amount of the solution up through the needle's hollow inner tube 70 and into the cavity. Preferably, the air previously drawn into the chamber separates the solution from the plunger's head 64, minimizing potential chemical degradation of either the plunger's head or the solution by contact with each other.

The platter 32 is then lowered to a position low enough to allow the vials 80, 82 to pass under the needle 52 without coming into contact with the needle, or any drop of solution that might be hanging from the needle. If a drop is visibly hanging from the needle, the stepper motor may further withdraw the plunger from the syringe to draw the drop into the needle. Preferably, the platter is lowered to its lowest position, where it cannot interfere with the laser micrometer 18 or block the view of the camera 20 during evaporation. The table 24 is then moved longitudinally such that the concentration port 100 of the heater 38 is directly below the needle 52 to provide for evaporation of the solvent in the solution, as is seen in FIG. 6C.

Once the heater's concentration port 100 is positioned below the needle 52, the laser micrometer takes an initial measurement of the diameter of any drop hanging from the contact surface 78 at the lower tip 74 of the needle. The measurement of the drop is relayed to the computerized control system, which preferably controls the stepper motor to draw the drop up into the needle. The heater is then preferably used to dry the exterior of the needle to prevent solution from later being pulled up the needle by surface tension forces.

Under the control of the computerized control system, the stepper motor 16 then causes the syringe 14 to produce a drop. The laser micrometer 18 measures the drop and compares the measurement with prescribed limits, being a prescribed minimum size and a prescribed maximum size. The prescribed maximum size is selected such that surface tension forces will reliably suspend the drop from the contact surface 78 at the lower tip of the needle.

The prescribed minimum size is selected to be large enough such that the suspended solution is in contact with sufficiently little solid material (i.e., on the contact surface) to avoid significant precipitation and plating of solute as the solvent evaporates. It is also selected to be large enough to provide an acceptably fast evaporation rate. The prescribed minimum size is selected to be small enough such that its difference from the maximum size is adequate to accommodate the tolerance of the stepper motor 16 (i.e., its ability to cause the emission of enough dilute solution to exceed the prescribed minimum size, but not to exceed the prescribed maximum size). Preferably, there is little or no change in the amount of contact area between the drop and the contact surface so long as the drop is between the minimum and maximum sizes, and thus the contact surface remains wet.

Under control of the control system, the stepper motor 16 advances the plunger to pass dilute solution out of the needle to the formed or forming drop, or retracts the plunger to draw solution from the drop into the needle, to adjust the size of the drop such that its measurement is greater than the prescribed minimum measurement and less than the prescribed maximum measurement. As before, the solution is passed out of the needle or drawn into the needle by moving the plunger 54 further into, or out of, the syringe body 50, respectively.

With the drop adjusted to be within the prescribed limits, the heater 38 is activated to create a column of heated gas flowing over the drop hanging from the needle 52. In particular, with reference to FIGS. 4A–4C, pressurized nitrogen gas is released from its supply (not shown), through the heater's inlet 94, through the main passage 96 and out through the concentration port 100. The heater element 98 is energized, which in turn heats the nitrogen gas as it passes through the main passage. The heater is configured to create a column of heated gas sufficient to cause evaporation of solvent from within the drop. While the above-described heater is the preferred embodiment of the heater, any device configured to accelerate the rate of the solvent's evaporation, whether through temperature, barometric pressure, or other relevant factors, is within the scope of the invention. While it is preferable that the heater is energized when the drop is within the prescribed limits, it is well within the scope of the invention to energize the heater prior to passing any solution out of the needle.

The column of heated gas evaporates some of the solvent within the drop, causing the volume of the drop to be reduced and the size of the drop to shrink. While the solvent within the drop is evaporating, the laser micrometer monitors the drop by continuing to measure the size of the drop. The measurements are relayed to the control system, which compares the measurements with the prescribed limits.

Returning to FIGS. 1A–1C and 2A–2B, when the size of the drop falls below the prescribed minimum, the control system instructs the stepper motor 16 to advance the plunger 54 into the syringe body 50, increasing the size of the drop to a size larger than the prescribed minimum. Preferably, the plunger is not advanced far enough to make the drop larger than the prescribed maximum size, as it is not preferable to draw concentrated solution back into the needle 52.

Preferably, the needle is configured to be narrow enough near the orifice to substantially prevent the concentrated solution from diffusing up the needle during the evaporation. Furthermore, the stepper motor and heater are preferably configured, and the prescribed minimum and maximum sizes are preferably chosen, to provide for evaporation and addition of solution to occur at a rate allowing near-continuous addition, so as to substantially prevent concentration gradient diffusion from the evaporating mixture as it becomes more concentrated.

The size of the drop is continuously monitored and adjusted until enough solvent has been evaporated to cause the drop to reach a prescribed concentration of solute in solution with the remaining solvent, or until all of the dilute solution in the syringe passes out into the drop. Depending on the desired concentration, it might be necessary to further concentrate the drop, reducing its size below the prescribed minimum. As the drop reaches the desired concentration, the heater is turned off, so as to stop or limit any further evaporation.

Little or no precipitation occurs on the contact surface 78 so long as the drop is maintained between the minimum and maximum sizes. Preferably, the contact surface is shaped, sized and oriented such that the contact area between it and the drop changes little (or not at all) if the drop is to be shrunk below the minimum size. For such a contact surface, little or no precipitation occurs on the contact surface even when the drop is reduced below the minimum size.

The resulting drop of concentrated solution may then be removed from the needle 52. In this embodiment, the concentrated solution is used to form a substantially uniform coating of solute plated within the source 110. Preferably, the drop of concentrated solution is removed from the needle by touching the bottom edge of the drop with the center of the source. Upon touching the source, the drop is drawn into the source through its perforations by capillary action, pulling the drop off of the needle.

The position of the source is adjusted to touch the drop through the use of the pick-off device's top adjustment screw 112, side adjustment screw 114, and front adjustment screw 116. While the above describes the preferred embodiment, a variety of pick off techniques are envisioned as within the scope of the invention. For example, an open end of the source can be touched to the side of the drop, drawing the drop into the end of the source by capillary forces.

As seen in FIGS. 5A–5B, the concentrated solution within the source 110 is then heated to evaporate the solvent, precipitating the solute and causing it to plate onto the source, forming a layer of solute in the interior of the source. To do so, the table is first laterally adjusted to position the heater's final-evaporation port 102 under the source. The heater valve 92 is then actuated to align the concentration-port valve's hole (see 106 in FIG. 4A) with the final-evaporation port. The nitrogen gas is again passed through the heater with the heater element energized, causing a band-shape, diffused column of heated air, which approximates the shape of the source, to rise up to the source and evaporate the last of the solvent.

EXAMPLE

An number of experimental runs have been made in the ambient conditions comprising an air temperature of 90–95° C. The syringe was configured with a needle having a 0.010 in. bore, which reduced to 0.005 in. at the lower tip (i.e., at the orifice). The needle also had a 0.090 in. outer diameter, which reduced to 0.070 in. at the lower tip.

A dilute solution of radioactive orthophosphoric acid in water, exhibiting approximately 1.5–2.0 $mCi/mm^3$ was used as the starting material. After the syringe was set up and adjusted, and was flushed and tested with water, 225 $mm^3$ of the dilute solution were drawn up into the syringe. The size of the suspended drop, which was estimated to have adequate surface tension forces to support a drop size up to 4 mm, was approximately maintained in the vicinity of 2.4 mm (±0.2) mm for safety. Upon heating, evaporation typically occurred at rates of 5 $mm^3$/min. At this rate, the fluid velocity through the orifice averaged 395 mm/min., effectively preventing diffusion back through the orifice. The volume of the concentrated drop was in the vicinity of 0.8 $mm^3$, which exhibited 200–350 mCi, and preferably 300 mCi.

The above-described method and apparatus embody a broad array of novel features of the invention. However, these features are not limited in scope by the described embodiments, as numerous other embodiments are within the scope of the invention. To demonstrate the breadth of the invention, a number of embodiment variations are discussed below.

The described embodiments characterize the solution as suspended in air. However the invention is equally applicable to any environment, gaseous or otherwise, that allows the solution to be suspended within it, and that can accommodate the removal of the solution's solvent, such as by evaporation.

Furthermore, the removal of the solution's solvent does not necessarily have to be accelerated by the addition of heat. Other environmental characteristics, such as pressure, may instead be varied to improve the evaporation rate. Indeed, the solvent could be allowed to evaporate without any stimulation, although it could greatly lengthen the necessary time for many embodiments.

Two aspects of the invention have been described as simultaneously used to minimize the precipitation of solute during evaporation. The first aspect is the suspension of the solution such that it is in contact with little surface area of a contact surface, providing for little or no change in the contact surface area. The second aspect is the addition of dilute solution to the globule of solution to maintain the volume of combined solution within a bound, providing for little or no change in the contact surface area. Each of these aspects may be used individually within the scope of the invention.

From the foregoing description, it will be appreciated that the present invention provides a method and apparatus to concentrate a solute in solution with a solvent, without the inefficiencies and problems associated with conventional evaporative systems. While particular forms of the invention have been illustrated and described, it will be apparent that various other modifications can be made without departing from the spirit and scope of the invention. Thus, although the invention has been described in detail with reference only to the preferred embodiments, those having ordinary skill in the art will appreciate that various modifications can be made without departing from the invention. Accordingly, the invention is not intended to be limited, and is defined with reference to the following claims.

We claim:

1. A method of concentrating a solute in a solution, said method comprising:

suspending a portion of said solution from a solid material, said solution consisting essentially of radioactive orthophosphoric acid in water;

evaporating a solvent from said suspended portion of said solution until said suspended portion reaches a predetermined concentration of said solute within said solution, said suspended portion being in contact with a predetermined amount of solid material, said amount chosen to avoid substantial precipitation of said solute during said evaporating; and adding additional solution to said suspended portion to maintain a predetermined amount of said suspended portion.

2. The method of claim 1, wherein the suspended portion is supported from said solid material by surface tension forces during said evaporating.

3. The method claim 1, wherein said adding further comprises passing the additional solution through an orifice of a container toward said suspended portion, said container to house said additional solution.

* * * * *

UNITED STATES PATENT AND TRADEMARK OFFICE
CERTIFICATE OF CORRECTION

PATENT NO.     : 6,391,149 B1
DATED          : May 21, 2002
INVENTOR(S)    : Calfee et al.

It is certified that error appears in the above-identified patent and that said Letters Patent is hereby corrected as shown below:

<u>Title page,</u>
Item [57] ABSTRACT,
Line 12, please delete "qualify" and insert -- quality --.

<u>Column 4,</u>
Line 34, after "motor", please delete ".".

<u>Column 5,</u>
Line 16, please delete "chambers" and insert -- chamber's --.

<u>Column 6,</u>
Line 9, please delete "Retuning" and insert -- Returning --.

Signed and Sealed this

Sixteenth Day of September, 2003

JAMES E. ROGAN
*Director of the United States Patent and Trademark Office*